US006821924B2

(12) United States Patent
Gulotty, Jr. et al.

(10) Patent No.: US 6,821,924 B2
(45) Date of Patent: Nov. 23, 2004

(54) OXYHALOGENATION PROCESS USING CATALYST HAVING POROUS RARE EARTH HALIDE SUPPORT

(75) Inventors: Robert J. Gulotty, Jr., Midland, MI (US); Mark E. Jones, Midland, MI (US); Daniel A. Hickman, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/706,545

(22) Filed: Nov. 12, 2003

(65) Prior Publication Data

US 2004/0097767 A1 May 20, 2004

Related U.S. Application Data

(62) Division of application No. 10/130,107, filed as application No. PCT/US00/31490 on Nov. 16, 2000, now Pat. No. 6,680,415.
(60) Provisional application No. 60/166,897, filed on Nov. 22, 1999.

(51) Int. Cl.$^7$ .......................... B01J 23/00; B01J 23/70; B01J 23/72; B01J 31/00; B01J 37/00
(52) U.S. Cl. ...................... 502/345; 502/102; 502/224; 502/225; 502/302; 502/303; 502/304; 502/344; 502/243; 570/243; 570/245; 570/224
(58) Field of Search ................................ 502/345, 224, 502/225, 102, 302, 303, 304, 344, 243; 570/243, 245, 224

(56) References Cited

U.S. PATENT DOCUMENTS

| 2,204,733 A | 6/1940 | Miller ........................ 23/219 |
| 3,149,171 A | 9/1964 | Arganbright ................ 260/655 |
| 3,488,398 A | 1/1970 | Harpring et al. ............ 260/659 |

(List continued on next page.)

FOREIGN PATENT DOCUMENTS

| DE | 237 058 A3 | 7/1986 |
| EP | 0 162 457 B1 | 7/1989 |
| EP | 0 720 975 A1 | 7/1996 |
| EP | 0 372 183 B1 | 1/1997 |
| EP | 0 667 845 B1 | 1/1998 |
| FR | 1 594 693 | 7/1970 |
| GB | 1 343 724 | 1/1874 |
| GB | 1 039 369 | 8/1966 |
| GB | 1 040 962 | 9/1966 |
| GB | 1 062 171 | 3/1967 |
| GB | 1 141 369 | 1/1969 |
| GB | 1 213 202 | 11/1970 |
| GB | 1 373 296 | 11/1974 |
| GB | 1 475 358 | 6/1977 |
| GB | 1 492 945 | 11/1977 |
| GB | 2 095 242 | 9/1982 |
| GB | 2 101 596 | 1/1993 |
| WO | 01/38272 | 5/2001 |
| WO | 01/38273 | 5/2001 |
| WO | 01/38274 | 5/2001 |
| WO | 01/38275 | 5/2001 |
| WO | 01/42176 | 6/2001 |
| WO | 02/094749 | 11/2002 |
| WO | 02/094750 A1 | 11/2002 |
| WO | 02/094751 A3 | 11/2002 |
| WO | 02/094752 | 11/2002 |

OTHER PUBLICATIONS

Au, C. T. et al., "The oxidative coupling of methane over $BaCO_3$/LaOCl catalysts", Applied Catalysis A: General, vol. 159 (1997) pp. 133–145.
Chanaud, P. et al., "Catalytic Membrane Reactor for Oxidative Coupling of Methane. Part 1: Preparation and Characterization of LaOCl Membranes", Catalysis Today, vol. 25 (1995) pp. 225–230.
Chanaud, P. et al., "Study of Lanthanum–based Colloidal Sols Formation", Journal of Materials Science, vol. 29 (1994) pp. 4244–4251.
Conner, Jr., Wm. Curtis et al., "The Oxyhydrochlorination of Methane on Fumed Silica–Based Cu, K, La Catalysts: III Bulk & Surface Analysis", Applied Catalysis, vol. 11 (1984) pp. 59–71.
Conner, Jr., Wm. C. et al., "The Oxyhydrochlorination of Methane on Fumed Silica–Based Cu, K, La Catalysts: II Gas Phase Stoichiometry", Applied Catalysis, vol. 11 (1984) pp. 49–58.
Fells, Ian, "The Kinetics of the Hydrolysis of the Chlorinate Methanes", Fuel Society Journal, vol. 10 (1959) pp. 26–35.
Fortini, E. M. et al., "Stabilization of the Active Phase by Interaction with the Support in $CuCl_2$ Oxychlorination Catalysts", Journal of Catalysis, vol. 99 (1965) pp. 12–18.
Lance, E. T. et al., "Preparation, Phase Equilibria, and Crystal Chemistry of Lanthanum, Praseodymium, and Neodymium Hydroxide Chlorides", Journal of Solid State Chemistry, vol. 17 (1976) pp. 55–60.
Lin, S. et al, "Oxidative Dehydrogenation of Ethane over Lanthanum–Substituted Layered Complex Bismuth Chloride Oxide Catalysts", The Chemical Society of Japan, Chemistry Letters (1997) pp. 901–902.

(List continued on next page.)

Primary Examiner—Elvis O. Price
(74) Attorney, Agent, or Firm—Marie F. Zuckerman

(57) ABSTRACT

An oxidative halogenation process involving contacting a hydrocarbon, for example, ethylene, or a halogenated hydrocarbon with a source of halogen, such as hydrogen chloride, and a source of oxygen in the presence of a catalyst so as to form a halocarbon, preferably a chlorocarbon, having a greater number of halogen substituents than the starting hydrocarbon or halogenated hydrocarbon, for example, 1,2-dichloroethane. The catalyst is a novel composition comprising copper dispersed on a porous rare earth halide support, preferably, a porous rare earth chloride support. A catalyst precursor composition comprising copper dispersed on a porous rare earth oxyhalide support is disclosed. Use of the porous rare earth halide and oxyhalide as support materials for catalytic components is disclosed.

16 Claims, No Drawings

U.S. PATENT DOCUMENTS

| | | | |
|---|---|---|---|
| 3,629,354 A | 12/1971 | Beard et al. | 260/683.3 |
| 3,634,330 A | 1/1972 | Yerres et al. | 252/441 |
| 3,644,561 A | 2/1972 | Beard et al. | 260/683.3 |
| 3,657,367 A | 4/1972 | Blake et al. | 260/659 A |
| 3,658,933 A | 4/1972 | Beard et al. | 260/683.3 |
| 3,658,934 A | 4/1972 | Beard et al. | 260/683.3 |
| 3,702,311 A | 11/1972 | Beard et al. | 252/441 |
| 3,769,362 A | 10/1973 | Beard et al. | 260/677 XA |
| 3,927,131 A | 12/1975 | Ward | 260/654 D |
| 3,968,178 A | 7/1976 | Obrecht et al. | 260/658 |
| 3,968,200 A | 7/1976 | Tsao | 423/488 |
| 4,025,461 A | 5/1977 | Croce et al. | 252/462 A |
| 4,042,640 A | 8/1977 | Tsao | 260/659 |
| 4,046,821 A | 9/1977 | Croce et al. | 260/654 |
| 4,046,823 A | 9/1977 | Gordon et al. | 260/662 R |
| 4,100,211 A | 7/1978 | Magistro | 260/656 R |
| 4,110,251 A | 8/1978 | Lauder et al. | 252/442 |
| 4,230,668 A | 10/1980 | Sheely et al. | 422/140 |
| 4,300,005 A | 11/1981 | Li | 570/224 |
| 4,319,062 A | 3/1982 | Boozalis et al. | 570/220 |
| 4,323,482 A | 4/1982 | Stiles et al. | 252/462 |
| 4,329,525 A | 5/1982 | Riegel et al. | 570/191 |
| 4,375,569 A | 3/1983 | Kroenke et al. | 570/224 |
| 4,402,942 A | 9/1983 | Melin | 424/177 |
| 4,405,500 A | 9/1983 | Muller et al. | 252/433 |
| 4,460,699 A | 7/1984 | Convers et al. | 502/84 |
| 4,462,970 A | 7/1984 | Pastor et al. | 423/263 |
| 4,523,040 A | 6/1985 | Olah | 568/671 |
| 4,528,174 A | 7/1985 | Schmidhammer et al. | 423/488 |
| 4,529,410 A | 7/1985 | Khaladji et al. | 51/309 |
| 4,590,216 A | 5/1986 | Dombek | 518/700 |
| 4,727,201 A | 2/1988 | Cobb | 570/202 |
| 4,737,594 A | 4/1988 | Olah | 570/222 |
| 4,754,088 A | 6/1988 | Schmidhammer et al. | 570/247 |
| 4,766,103 A | 8/1988 | Cobb | 502/217 |
| 4,769,504 A | 9/1988 | Noceti et al. | 585/415 |
| 4,783,564 A | 11/1988 | Piotrowski et al. | 570/254 |
| 4,849,393 A * | 7/1989 | Eden et al. | 502/225 |
| 4,849,562 A | 7/1989 | Buhs et al. | 570/241 |
| 4,859,432 A | 8/1989 | David et al. | 423/21.1 |
| 4,899,000 A | 2/1990 | Stauffer | 570/222 |
| 4,942,697 A | 7/1990 | Khaladji et al. | 51/283 R |
| 4,965,057 A | 10/1990 | David et al. | 423/263 |
| 5,008,225 A | 4/1991 | Magistro | 502/73 |
| 5,013,534 A | 5/1991 | Dissaux et al. | 423/263 |
| 5,023,070 A | 6/1991 | Le Loarer | 423/592 |
| 5,061,670 A | 10/1991 | Forquy et al. | 585/500 |
| 5,072,063 A | 12/1991 | Langensee | 570/236 |
| 5,087,791 A | 2/1992 | Magistro | 585/657 |
| 5,097,083 A | 3/1992 | Stauffer | 570/241 |
| 5,099,085 A | 3/1992 | Strasser et al. | 570/245 |
| 5,113,027 A | 5/1992 | Mainz et al. | 570/224 |
| 5,114,702 A | 5/1992 | Pederson et al. | 423/639 |
| 5,137,862 A | 8/1992 | Mackrodt et al. | 502/303 |
| 5,178,664 A | 1/1993 | Picard | 75/300 |
| 5,179,215 A | 1/1993 | Ramachandran et al. | 549/262 |
| 5,210,358 A | 5/1993 | Magistro | 585/503 |
| 5,227,549 A | 7/1993 | Correia et al. | 570/243 |
| 5,232,889 A | 8/1993 | Blanchard et al. | 502/263 |
| 5,262,547 A | 11/1993 | Ramachandran et al. | 549/262 |
| 5,352,646 A | 10/1994 | Blanchard et al. | 502/263 |
| 5,397,758 A | 3/1995 | Bouruetaubertot et al. | 502/303 |
| 5,453,557 A | 9/1995 | Harley et al. | 585/641 |
| 5,466,837 A | 11/1995 | Ramachandran et al. | 549/533 |
| 5,492,878 A | 2/1996 | Fujii et al. | 502/304 |
| 5,496,528 A | 3/1996 | David et al. | 423/263 |
| 5,510,546 A | 4/1996 | Ito | 570/236 |
| 5,580,536 A | 12/1996 | Yao et al. | 423/263 |
| 5,599,588 A | 2/1997 | Poncelet | 427/343 |
| 5,600,042 A | 2/1997 | Chen et al. | 570/230 |
| 5,607,890 A | 3/1997 | Chen et al. | 205/202 |
| 5,646,304 A | 7/1997 | Acharya et al. | 549/259 |
| 5,663,112 A | 9/1997 | Ahn et al. | 502/304 |
| 5,663,465 A | 9/1997 | Clegg et al. | 570/224 |
| 5,663,472 A | 9/1997 | Benson et al. | 585/641 |
| 5,705,728 A | 1/1998 | Viswanathan et al. | 585/641 |
| 5,728,905 A | 3/1998 | Clegg et al. | 570/224 |
| 5,762,894 A | 6/1998 | Takatori et al. | 423/263 |
| 5,763,710 A | 6/1998 | Clegg et al. | 570/224 |
| 5,773,383 A | 6/1998 | Suciu | 502/355 |
| 5,874,380 A | 2/1999 | Chen et al. | 502/217 |
| 5,877,371 A | 3/1999 | Chen et al. | 585/467 |
| 5,880,058 A | 3/1999 | Moriya et al. | 502/302 |
| 5,883,037 A | 3/1999 | Chopin et al. | 502/308 |
| 5,898,014 A | 4/1999 | Wu et al. | 502/302 |
| 5,905,177 A | 5/1999 | Seo et al. | 570/243 |
| 5,919,727 A | 7/1999 | Brezny | 502/304 |
| 5,922,639 A | 7/1999 | Alario et al. | 502/230 |
| 5,925,590 A | 7/1999 | White et al. | 502/302 |
| 5,935,897 A | 8/1999 | Trubenbach et al. | 502/527.14 |
| 5,935,898 A | 8/1999 | Trubenbach et al. | 502/527.14 |
| 5,945,370 A | 8/1999 | Yokoi et al. | 502/304 |
| 5,945,573 A | 8/1999 | Nappa et al. | 570/175 |
| 5,955,638 A | 9/1999 | Schoebrechts et al. | 570/232 |
| 5,969,195 A | 10/1999 | Stabel et al. | 568/700 |
| 5,972,827 A | 10/1999 | Petit et al. | 502/225 |
| 5,972,830 A | 10/1999 | Yoshida et al. | 502/304 |
| 5,994,260 A | 11/1999 | Bonneau et al. | 502/304 |
| 6,002,019 A | 12/1999 | Tamhankar et al. | 549/285 |
| 6,090,743 A | 7/2000 | Chopin et al. | 502/302 |
| 6,136,048 A | 10/2000 | Birchem et al. | 44/354 |
| 6,165,931 A | 12/2000 | Rao | 502/224 |
| 6,191,329 B1 | 2/2001 | Benje | 570/243 |
| 6,194,345 B1 | 2/2001 | Mangnus et al. | 502/224 |
| 6,228,799 B1 | 5/2001 | Aubert et al. | 502/304 |
| 6,452,058 B1 | 9/2002 | Schweizer et al. | 570/223 |

OTHER PUBLICATIONS

McDonald, Mark A. et al., "Effects of Pressure on the Oxyhydrochlorination of Methane", Chemical Engineering Science, vol. 49, No. 24A (1994) pp. 4627–4637.

Miyake, Takanori et al., "Screening of Metal Chloride Catalysts for Oxychlorination of Propene", Applied Catalysis A: General, vol. 121, No. 1 (1995) pp. L13–L17.

Noceti, Richard P. et al., "Advances in Methane Oxyhydrochlorination Catalysts", Preprints, American Chemical Society, Washington, DC (1992) pp. 281–283.

Olah, George A. et al., "Selective Monohalogenation of Methane over Supported Acid or Platinum Metal Catalysts and Hydrolysis of Methyl Halides over Γ–Alumina–Supported Metal Oxide/Hydroxide Catalysts. A Feasible Path for the Oxidative Conversion of Methane into Methyl Alcohol/Dimethyl Ether", American Chemical Society, vol. 107, No. 24 (1985) pp. 7097–7105.

Patent Abstracts of Japan, vol. 004, No. 190 (Dec. 26, 1980) (Corresponds to JP 55 130923).

Pieters, W.J.M. et al., "The Oxyhydrochlorination of Methane on Fumed Silica—Based $Cu^{+1}$, K, La Catalysts: I. Catalyst Synthesis", Applied Catalysis, vol. 11 (1984) pp. 35–48.

Poznanski, J., "A Study of the Chlorination of Lanthanum and Neodymium Oxides", Materials Science, XVIII (1992) pp. 99–104.

Weckhuysen, Bert M. et al., "Destructive Absorption of Carbon Tetrachloride on Lanthanum and Cerium Oxides", Phys. Chem. Chem. Phys., vol. 1, (1999) pp. 3157–3162.

Weissemel, K. et al., Industrial Organic Chemistry, $2^{nd}$ Edition, VCH, Weinheim (1993) pp. 168–175.

Derwent Publication, AN 1978–85275A, "Allyl chloride prepn. from propylene, hydrogen chloride and oxygen—using catalyst comprising chloride of samarium, chromium, manganese or praseodymium", Research Disclosure RD–175041, Anonymous.

"Process for Vinyl Chloride Manufacture from Ethane and Ethylene with Secondary Reactive Consumption of Reactor Effluent HCl", filed in the United States Receiving Office on May 14, 2002, USSN 10/130,105, Applicant: Mark E. Jones et al. (Corresponds to WO 01/38272).

"Production of Vinyl Halide from Single Carbon Feedstocks", filed in the United States Receiving Office on Nov. 18, 2003, USSN 10/130,105, Applicant: Mark E. Jones et al. (Corresponds to WO 02/09749).

"Process for Vinyl Chloride Manufacture from Ethane and Ethylene with Air Feed and Alternative HCl Processing", filed in the United States Receiving Office on Nov. 11, 2003, USSN 10/477,502, Applicant: William D. Clarke et al. (Corresponds to WO 02/094752).

"Dehydrogenation of Halogenated Alkanes Using Rare Earth Halide or Oxyhalide Catalyst", filed in the United States Receiving Office on May 14, 2002, USSN 10/130,106, Applicant: Larry N. Ito et al. (Corresponds to WO 01/38275).

"Oxidative Halogenation and Optional Dehydrogenation of C3+ Hydrocarbons", filed in the United States Receiving Office on Nov. 18, 2003, USSN 10/478,265, Applicant: Albert E. Schweizer et al. (Corresponds to WO 02/094750).

"A Process for the Conversion of Ethylene to Vinyl Chloride, and Novel Catalyst Compositions Useful for Such Process", filed in the United States Receiving Office on May 14, 2002, USSN 10/130,104, Applicant: Mark E. Jones et al. (Corresponds to WO 01/38273).

"Process for Vinyl Chloride Manufacture From Ethane and Ethylene with Partial HCl Recovery From Reactor Effluent", filed in the United States Receiving Office on May 14, 2002, USSN 10/130,102, Applicant: John P. Henley et al. (Corresponds to WO 01/42176).

"Process for Vinyl Chloride Manufacture From Ethane and Ethylene with Partial HCl Recovery From Reactor Effluent", filed in the United States Receiving Office on May 14, 2002, USSN 10/130,103, Applicant: Daniel A. Hickman et al. (Corresponds to WO 01/38274).

* cited by examiner

OXYHALOGENATION PROCESS USING CATALYST HAVING POROUS RARE EARTH HALIDE SUPPORT

CROSS-REFERENCE TO RELATED APPLICATIONS

This application is a divisional of U.S. application Ser. No. 10/130,107 filed May 14, 2002, now U.S. Pat. No. 6,680,415, which is a 371 continuation of PCT Application PCT/US00/31490 filed Nov. 16, 2000, which claims the benefit of U.S. Provisional Application No. 60/166,897, filed Nov. 22, 1999.

BACKGROUND OF THE INVENTION

In a first aspect, this invention pertains to a process of oxidative halogenation, particularly oxidative chlorination. For the purposes of this discussion, the term "oxidative halogenation" is defined as a process wherein a hydrocarbon or halogenated hydrocarbon (the "starting hydrocarbon") is contacted with a source of halogen and a source of oxygen so as to form a halocarbon having a greater number of halogen substituents than the starting hydrocarbon. The term "halocarbon" will include halogenated hydrocarbons as well as compounds consisting only of carbon and halogen atoms. In a second aspect, this invention pertains to a novel catalyst for the oxidative halogenation process. In a third aspect, this invention pertains to novel catalyst supports.

Halogenated hydrocarbons, such as 1,2-dichloroethane, 1,2-dibromoethane, dichloropropanes, and dichloropropenes, find utility in numerous applications, such as in fumigants and in the production of monomers useful in polymerization processes. 1,2-Dichloroethane, for example, which is manufactured industrially on a scale of several million tons per year, is converted by thermal dehydrochlorination into vinyl chloride monomer(VCM) and hydrogen chloride. VCM is polymerized into poly(vinyl)chloride (or PVC), a widely used polymer. The hydrogen chloride produced by dehydrochlorination is separated from the VCM and thereafter contacted with ethylene and oxygen in the presence of a catalyst to produce 1,2-dichloroethane. In the prior art, the contacting specifically of ethylene, hydrogen chloride, and oxygen to form 1,2-dichloroethane and water is known as the "oxychlorination reaction."

The oxychlorination of ethylene is abundantly described in the patent literature, representative art of which includes U.S. Pat. Nos. 3,634,330, 3,658,367, 3,658,934, 5,972,827, GB 1,039,369, and GB 1,373,296. The catalyst employed in the oxychlorination of ethylene typically contains copper chloride or iron chloride, and optionally, one or more alkali or alkaline earth metal chlorides, and/or optionally, one or more rare earth chlorides, supported on an inert carrier, typically alumina, silica, or an aluminosilicate. Alternatively, the catalyst components can be unsupported, but fused into a molten salt.

Oxidative halogenation processes are quite general and can be extended to a variety of hydrocarbons in addition to ethylene. For example, oxidative chlorination processes are known for the conversion of methane to chloromethanes, ethane to chloroethanes and chloroethenes, and, by analogy, higher saturated hydrocarbons to higher chlorohydrocarbons. This chemistry is not unique to chlorine and can also be extended broadly to other halogens. Halogen sources can comprise hydrogen halides and halohydrocarbons having labile halogens.

One disadvantage of prior art oxidative halogenation processes involves their production of undesirable oxygenated by-products, such as partially oxidized hydrocarbons and deep oxidation products ($CO_x$), namely, carbon monoxide and carbon dioxide. Another disadvantage of prior art oxidative halogenation processes involves their production of undesirable oxygenated halocarbon by-products, for example, trichloroacetaldehyde (also known as chloral, $CCl_3CHO$) in the production of 1,2-dichloroethane. The production of unwanted by-products irretrievably wastes the hydrocarbon feed and creates product separation and by-product disposal problems. Any reduction in the quantity of oxygenated products, particularly, oxygenated halocarbons and $CO_x$ oxygenates would be highly desirable.

In a different aspect, rare earth compounds are known to be promoters in a diverse assortment of catalyzed organic processes, including, for example, oxidations, steam reforming, auto emission reduction, esterification, Fischer-Tropsch synthesis, and the aforementioned oxidative halogenation processes. In the general preparation of rare earth-promoted catalysts, a solution containing a soluble rare earth salt, such as the chloride, is dispersed, for example, by impregnation or ion-exchange, optionally, along with one or more additional catalytic components onto a support or carrier, such as alumina or silica. U.S. Pat. No. 2,204,733 discloses a catalyst containing a compound of copper and a compound of the rare earth group, being prepared by pre-cipitating the metals as hydroxides onto a suitable support, or by soaking or impregnating a support with a solution of copper and rare earth salts, or by precipitating the metals as hydroxides with sodium or potassium hydroxide. The art, in general, appears to be silent with respect to rare earth compounds functioning as catalyst carriers or supports, perhaps because rare earth compounds typically are not found to be porous. Catalyst supports are generally known to require at least some porosity, that is, some void space, such as channels and pores or cavities, which create surface area whereon catalytic metals and components can be deposited.

SUMMARY OF THE INVENTION

In one aspect, this invention is a novel oxidative halogenation process of preparing a halocarbon. The novel process of this invention comprises contacting a hydrocarbon or halogenated hydrocarbon with a source of halogen and a source of oxygen in the presence of a catalyst under process conditions sufficient to prepare a halocarbon containing a greater number of halogen substituents than in the starting hydrocarbon or halogenated hydrocarbon, as the case may be, the catalyst comprising copper on a porous rare earth halide support. The term "halocarbon" will be understood as including halogenated hydrocarbons as well as compounds consisting only of carbon and halogen atoms.

The oxidative halogenation process of this invention advantageously converts a hydrocarbon or halogenated hydrocarbon in the presence of a source of halogen and a source of oxygen into a halocarbon having an increased number of halogen substituents as compared with the starting hydrocarbon. Accordingly, the process of this invention can be used, in a preferred embodiment, to oxychlorinate ethylene in the presence of hydrogen chloride and oxygen into 1,2-dichloroethane. Since the hydrogen chloride may be derived from the dehydrochlorination of 1,2-dichloroethane, the process of this invention may be easily integrated into a VCM plant, as described hereinabove. As a more preferred advantage, the process of this invention produces lower levels of undesirable by-products, particularly $CO_x$ oxygenates, namely, carbon monoxide and carbon dioxide, and lower levels of undesirable oxygenated halocarbons, such as chloral, than prior art oxidative halogenation processes. The reduction in undesirable oxygenated by-products translates into a higher selectivity to the desired halocarbon product, lower waste of hydrocarbon feed, and fewer by-product disposal problems. In addition, the better selectivity to the desired halocarbon product allows the process to be operated at higher temperatures for higher conversion.

In a second aspect, this invention is a novel composition of matter comprising copper dispersed on a porous rare earth halide support.

The novel composition of this invention is useful as a catalyst in the oxidative halogenation of hydrocarbons or halogenated hydrocarbons, as exemplified by the oxychlorination of ethylene in the presence of a source of chlorine and oxygen to form 1,2-dichloroethane. Advantageously, the novel catalyst of this invention produces lower levels of by-products, particularly $CO_x$ oxygenates and oxygenated halocarbons, such as chloral, in the aforementioned oxidative halogenation process. As a second advantage, the unique catalyst composition of this invention does not require a conventional carrier or support, such as alumina or silica. Rather, the catalyst of this invention employs a porous rare earth halide, which uniquely functions both as the catalyst's support and as a source of a further catalytically active (rare earth) component.

In a third aspect, this invention is a second composition of matter comprising copper dispersed on a porous rare earth oxyhalide support. This second novel composition is a useful catalyst precursor to the catalyst comprising copper dispersed on the porous rare earth halide support, described hereinabove.

In a fourth aspect, this invention claims use of the aforementioned porous rare earth oxyhalide and porous rare earth halide as supports and carriers for catalytic components. The porous rare earth oxyhalide or rare earth halide can be used as a support for any catalytic metal or metallic ion in the Periodic Table of the Elements, as well as any organic or non-metallic inorganic catalyst component.

The porous rare earth oxyhalide or halide support can be advantageously employed in catalysts which benefit from the promoting effects of rare earth elements and/or in catalysts which require basicity. Unlike most catalyst supports of the prior art, the rare earth halide support of this invention is soluble in water. Accordingly, should process equipment, such as filters, valves, circulating tubes, and small or intricate parts of reactors, become plugged with particles of a catalyst containing the rare earth halide support of this invention, then a simple water wash can advantageously dissolve the plugged particles and restore the equipment to working order. As a further advantage, the novel rare earth halide and oxyhalide supports of this invention provide for the easy recovery of costly catalytic metals. The recovery simply involves contacting the spent catalyst containing the catalytic metals and the novel support with acid under conditions sufficient to etch away the catalytic metals. Thereafter, the metals can be recovered from the acidic medium, for example, by precipitation. Any portion of the rare earth support dissolved into the acidic medium can also be recovered by re-precipitation with base.

DETAILED DESCRIPTION OF THE INVENTION

In the novel oxidative halogenation process of this invention, a halocarbon is produced selectively with advantageously low levels of by-products, such as, $CO_x$ oxygenates ($CO$ and $CO_2$) and oxygenated halocarbons, such as, chloral. The novel process of this invention comprises contacting a hydrocarbon or halogenated hydrocarbon (the "starting hydrocarbon") with a source of halogen and a source of oxygen in the presence of a catalyst under process conditions sufficient to prepare a halocarbon having a greater number of halogen substituents than the starting hydrocarbon. As mentioned hereinbefore, for the purposes of this invention, the term "halocarbon" includes halogenated hydrocarbons, such as 1,2-dichloroethane, as well as compounds consisting only of carbon and halogen atoms, such as perchloroethylene.

In a preferred embodiment, the process of this invention is an oxidative chlorination process comprising contacting a hydrocarbon or chlorinated hydrocarbon with a source of chlorine and a source of oxygen in the presence of a catalyst under conditions sufficient to prepare a chlorocarbon having a greater number of chloro substituents than in the starting hydrocarbon. In a most preferred embodiment of this invention, the hydrocarbon is ethylene, and the chlorocarbon is 1,2-dichloroethane.

The novel catalyst employed in the oxidative halogenation process of this invention comprises copper dispersed on a porous rare earth halide support. For the purposes of this invention, porosity is expressed in terms of surface area. In a preferred embodiment, the porous rare earth halide support has a surface area of least 5 $m^2/g$, as determined by the BET (Brunauer-Emmet-Teller) method of measuring surface area, as described by S. Brunauer, P. H. Emmett, and E. Teller, *Journal of the American Chemical Society,* 60, 309 (1938). In a preferred embodiment, the porous rare earth halide support comprises a porous rare earth chloride.

In another aspect, this invention is a second composition of matter comprising copper dispersed on a porous rare earth oxyhalide support. This second composition functions as a catalyst precursor, which finds utility in the preparation of the aforementioned rare earth halide catalyst. In a preferred embodiment, the porous rare earth oxyhalide support has a surface area of least 12 $m^2/g$, as determined by the BET method. In a more preferred embodiment, the porous rare earth oxyhalide support comprises a rare earth oxychloride.

In yet another aspect, this invention claims the use of the aforementioned porous rare earth oxyhalide and porous rare earth halide as a support or carrier for catalytic components.

Hereinafter, the description will be drafted towards the preferred process of oxidative chlorination; however, in light of the detailed description set forth, one skilled in the art will be able to extend the description to oxidative halogenations other than oxidative chlorination.

The hydrocarbon used in the oxidative chlorination process of this invention may be any hydrocarbon which is capable of acquiring halogen substituents in accordance with the process of this invention. The hydrocarbon may be an essentially pure hydrocarbon or a mixture of hydrocarbons. The hydrocarbon may be $C_{1-20}$ aliphatic hydrocarbons, including $C_{1-20}$ alkanes or $C_{2-20}$ alkenes, as well as $C_{3-12}$ cycloaliphatic hydrocarbons, or $C_{6-15}$ aromatic hydrocarbons. Suitable non-limiting examples of such hydrocarbons include methane, ethane, propane, ethylene, propylene, butanes, butenes, pentanes, pentenes, hexanes, hexenes, cyclohexane and cyclohexene, as well as benzene and other $C_{6-15}$ aromatics, such as naphthalenes. More preferably, the hydrocarbon is selected from $C_{1-20}$ aliphatic hydrocarbons, even more preferably, from $C_{2-10}$ alkenes, and most preferably, ethylene.

It is further within the scope of this invention for the hydrocarbon feed to be substituted with one or more halogen substituents. Preferably, however, the substituted hydrocarbon retains at least one or more carbon-hydrogen bonds; but as noted hereinbelow, certain halocarbons that do not contain carbon-hydrogen bonds, such as (perhalo)olefins, may also be suitable. Preferred halogen substituents include fluorine, chlorine, and bromine. More preferred, are fluorine and chlorine. As an example, the starting halogenated hydrocarbon can be a fluorohydrocarbon which is converted via the oxidative chlorination process of this invention into a chlorofluorocarbon. In an alternative embodiment, a (perfluoro)olefin can be employed as the starting material and converted into a chlorofluorocarbon.

The source of chlorine, which is employed in the process of this invention, can be any chlorine-containing compound, which is capable of transferring its chlorine to the hydrocarbon feed and providing a source of hydrogen to the oxygen feed. Suitable non-limiting examples of the source of chlorine include hydrogen chloride and any chlorinated hydrocarbon having one or more labile chlorine substituents (that is, transferable chloro substituents), a non-limiting example of which is methylene dichloride. Typically, molecular chlorine ($Cl_2$) is not employed in the process of this invention, which requires a source of oxygen and produces water. Preferably, the source of chlorine is hydrogen chloride.

The source of chlorine may be provided to the process in any amount which is effective in producing the desired chlorocarbon product. Typically, the source of chlorine is used in an amount equal to the stoichiometric amount required by the oxidative chlorination reaction of interest. In the oxychlorination of ethylene with hydrogen chloride and oxygen, for example, the theoretical stoichiometry is the following:

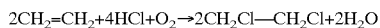

$$2CH_2=CH_2+4HCl+O_2 \rightarrow 2CH_2Cl\text{---}CH_2Cl+2H_2O$$

Consequently, in ethylene oxychlorination according to this invention, typically four moles of hydrogen chloride are employed per mole of oxygen. The hydrogen chloride and oxygen are employed in amounts which are ideally selected to facilitate the near complete reaction of both reagents; but greater and lesser amounts of hydrogen chloride may also be found suitable.

The source of oxygen can be any oxygen-containing gas, such as, commercially pure molecular oxygen, or air, or a mixture of oxygen in another diluent gas which does not interfere with the oxychlorination process, these being mentioned hereinafter. Generally, the feed to the oxidative chlorination reactor is "fuel-rich," meaning that a molar excess of starting hydrocarbon is used relative to oxygen. Typically, the molar ratio of starting hydrocarbon to oxygen is greater than 2/1, preferably, greater than 4/1, and more preferably, greater than 5/1. Typically, the molar ratio of hydrocarbon to oxygen is less than 20/1, preferably, less than 15/1, and more preferably, less than 10/1.

Optionally, if desired, the feed, comprising starting hydrocarbon, source of halogen, and source of oxygen, can be diluted with a diluent or carrier gas, which may be any gas that does not substantially interfere with the oxidative chlorination process. The diluent may assist in removing products and heat from the reactor and in reducing the number of undesirable side-reactions. Non-limiting examples of suitable diluents include nitrogen, argon, helium, carbon monoxide, carbon dioxide, methane, and mixtures thereof. The quantity of diluent employed typically ranges from greater than 10 mole percent, and preferably, greater than 20 mole percent, to typically, less than 90 mole percent, and preferably, less than 70 mole percent, based on the total moles of feed to the reactor, that is, total moles of starting hydrocarbon, source of halogen, source of oxygen, and diluent.

From the foregoing discussion the feedstream to the oxidative chlorination process comprises a mixture of hydrocarbon or halogenated hydrocarbon, a source of chlorine, a source of oxygen, and optionally, a diluent or carrier gas. Accordingly, due diligence should be taken to avoid explosive mixtures. Towards this end, one skilled in the art would know how to thoroughly evaluate the flammability limits of the specific feedstream employed.

In a second aspect of the present invention, there is provided a composition of matter which is useful as a catalyst in the aforementioned oxidative chlorination process. The composition comprises copper dispersed on a porous rare earth halide support. The rare earths are a group of 17 elements consisting of scandium (atomic number 21), yttrium (atomic number 39) and the lanthanides (atomic numbers 57–71) [James B. Hedrick, U.S. Geological Survey—Minerals Information—1997, "Rare-Earth Metals"]. Preferably, herein, the term is taken to mean an element selected from lanthanum, cerium, neodymium, praseodymium, dysprosium, samarium, yttrium, gadolinium, erbium, ytterbium, holmium, terbium, europium, thulium, lutetium, and mixtures thereof. Preferred rare earth elements for use in the aforementioned oxidative chlorination process are those which are typically considered as being single valency metals. Catalytic performance of porous rare earth halide-supported catalysts using multi-valency metals appears to be less desirable than those using single valency metals. The rare earth element for this invention is preferably selected from lanthanum, neodymium, praseodymium, and mixtures thereof. Most preferably, the rare earth element used in the catalyst support is lanthanum or a mixture of lanthanum with other rare earth elements.

Preferably, the support is represented by the formula $MX_3$ wherein M is at least one rare earth element lanthanum, cerium, neodymium, praseodymium, dysprosium, samarium, yttrium, gadolinium, erbium, ytterbium, holmium, terbium, europium, thulium, lutetium, and mixtures thereof; and wherein X is chloride, bromide, or iodide. More preferably, X is chloride, and the more preferred support is represented by the formula $MCl_3$, wherein M is defined hereinbefore. Most preferably, X is chloride and M is lanthanum, and the rare earth halide support is lanthanum chloride.

Typically, the porous rare earth halide support has a BET surface area greater than 5 $m^2/g$, preferably, greater than 10 $m^2/g$, more preferably, greater than 15 $m^2/g$, even more preferably, greater than 20 $m^2/g$, and most preferably, greater than 30 $m^2/g$. For these above measurements, the nitrogen adsorption isotherm was measured at 77K and the surface area was calculated from the isotherm data utilizing the BET method.

In a third aspect of the present invention, there is provided a composition which is useful as a catalyst precursor to the aforementioned rare earth halide supported catalyst composition. The catalyst precursor comprises copper dispersed on a porous rare earth oxyhalide support. Preferably, the support is represented by the formula MOX, wherein M is at least one rare earth element lanthanum, cerium, neodymium, praseodymium, dysprosium, samarium, yttrium, gadolinium, erbium, ytterbium, holmium, terbium, europium, thulium, lutetium, or mixtures thereof; and wherein X is chloride, bromide, or iodide. More preferably, the support is a rare earth oxychloride, represented by the formula MOCl, wherein M is defined hereinbefore. Most preferably, the rare earth oxychloride is lanthanum oxychloride, LaOCl.

Typically, the porous rare earth oxyhalide support has a BET surface area of greater than 12 $m^2/g$, preferably, greater than 15 $m^2/g$, more preferably, greater than 20 $m^2/g$, and most preferably, greater than 30 $m^2/g$. Generally, the BET surface area is less than 200 $m^2/g$. In addition, it is noted that the MOCl phases possess characteristic powder X-Ray Diffraction (XRD) patterns that are distinct from the $MCl_3$ phases.

In one preferred embodiment of this invention, the catalyst and catalyst precursor compositions are essentially free of alumina, silica, aluminosilicate, and other conventional refractory support materials, for example, titania or zirconia. The term "essentially free" means that the conventional support material is present in a quantity less than 1 weight percent, more preferably, less than 0.5 weight percent, and most preferably, less than 0.1 weight percent, based on the total weight of the catalyst or catalyst precursor composition and conventional support material.

In an alternative embodiment of this invention, the catalyst or catalyst precursor composition, described hereinbefore (including copper on a rare earth halide or rare earth oxyhalide support material), may be bound to, extruded with, or deposited onto a conventional support, such as alumina, silica, silica-alumina, porous aluminosilicate (zeolite), silica-magnesia, bauxite, magnesia, silicon carbide, titanium oxide, zirconium oxide, zirconium silicate, or combination thereof. In this embodiment, the conventional support is used in a quantity greater than 1 weight percent, but less than 50 weight percent, preferably, less than 30 weight percent, more preferably, less than 20 weight percent, based on the total weight of the catalyst or catalyst precursor composition and conventional support. Even when a conventional support is present, it is still a fact that the copper is predominantly deposited on the rare earth oxyhalide or halide support and that the rare earth oxyhalide or halide support remains the predominant bulk material.

It may also be advantageous to include other elements within the catalyst. For example, preferable elemental additives include alkali and alkaline earths, boron, phosphorous, sulfur, germanium, titanium, zirconium, hafnium, and combinations thereof. These elements can be present to alter the catalytic performance of the composition or to improve the mechanical properties (for example, attrition-resistance) of the material. In a most preferred embodiment, however, the elemental additive is not aluminum or silicon. The total concentration of elemental additives in the catalyst is typically greater than 0.01 weight percent and typically less than 20 weight percent, based on the total weight of the catalyst.

In light of the disclosure herein, those of skill in the art will recognize alternative methods for preparing the support composition of this invention. A method currently felt to be preferable for forming the composition comprising the porous rare earth oxyhalide (MOX) comprises the following steps: (a) preparing a solution of a halide salt of the rare earth element or elements in a solvent comprising either water, an alcohol, or mixtures thereof; (b) adding a base to cause the formation of a precipitate; and (c) collecting and calcining the precipitate in order to form the MOX. Preferably, the halide salt is a rare earth chloride salt, for example, any commercially available rare earth chloride. Typically, the base is a nitrogen-containing base selected from ammonium hydroxide, alkyl amines, aryl amines, arylalkyl amines, alkyl ammonium hydroxides, aryl ammonium hydroxides, arylalkyl ammonium hydroxides, and mixtures thereof. The nitrogen-containing base may also be provided as a mixture of a nitrogen-containing base with other bases that do not contain nitrogen. Preferably, the nitrogen-containing base is ammonium hydroxide or tetra(alkyl)ammonium hydroxide, more preferably, tetra($C_{1-20}$ alkyl)ammonium hydroxide. Porous rare earth oxychlorides may also be produced by appropriate use of alkali or alkaline earth hydroxides, particularly, with the buffering of a nitrogen-containing base, although caution should be exercised to avoid producing the rare earth hydroxide or oxide. The solvent in Step (a) is preferably water. Generally, the precipitation is conducted at a temperature greater than 0° C. Generally, the precipitation is conducted at a temperature less than 200° C., preferably, less than 100° C. The precipitation is conducted generally at ambient atmospheric pressure, although higher pressures may be used, as necessary, to maintain liquid phase at the precipitation temperature employed. The calcination is typically conducted at a temperature greater than 200° C., preferably, greater than 300° C., and less than 800° C., preferably, less than 600° C. Production of mixed carboxylic acid and rare earth chloride salts also can yield rare earth oxychlorides upon appropriate decomposition.

A method currently felt to be preferable for forming the catalyst composition comprising the rare earth halide ($MX_3$) comprises the following steps: (a) preparing a solution of a halide salt of the rare earth element or elements in a solvent comprising either water, an alcohol, or mixtures thereof; (b) adding a base to cause the formation of a precipitate; (c) collecting and calcining the precipitate; and (d) contacting the calcined precipitate with a halogen source. Preferably, the rare earth halide is a rare earth chloride salt, such as any commercially available rare earth chloride. The solvent and base may be any of those mentioned hereinbefore in connection with the formation of MOX. Preferably, the solvent is water, and the base is a nitrogen-containing base. The precipitation is generally conducted at a temperature greater than 0° C. and less than 200° C., preferably less than 100° C., at ambient atmospheric pressure or a higher pressure so as to maintain liquid phase. The calcination is typically conducted at a temperature greater than 200° C., preferably, greater than 300° C., but less than 800° C., and preferably, less than 600° C. Preferably, the halogen source is a hydrogen halide, such as hydrogen chloride, hydrogen bromide, or hydrogen iodide. More preferably, the halogen source is hydrogen chloride. The contacting with the halogen source is typically conducted at a temperature greater than 100° C. and less than 500° C. Typical pressures for the contacting with the source of halogen range from ambient atmospheric pressure to pressures less than 150 psia (1,034 kPa).

As noted hereinabove, the rare earth oxyhalide support (MOX) can be converted into the rare earth halide support ($MX_3$) by treating the MOX support with a source of halogen. Since the oxidative chlorination process of this invention requires a source of chlorine, it is possible to contact the Cu-loaded MOCl support with a source of chlorine in situ in the oxidative chlorination reactor to form the $MCl_3$-supported Cu catalyst. The in situ method of forming the catalyst can be generalized to halogen species other than chlorine. The porous rare earth oxyhalide material also finds utility as a catalyst support, even under conditions which do not convert the oxyhalide to the halide.

The porous oxychloride material, MOX, and the fully chlorided material, $MX_3$, can be used in any process wherein a catalyst support or carrier is required. The porous rare earth oxyhalide or halide can be used as a support for any catalytic metal or metallic ion in the Periodic Table of the Elements, as well as any organic or non-metallic inorganic catalyst component. Suitable metals and metallic ions can be selected from Groups 1A, 2A, 3B, 4B, 5B, 6B, 7B, 8B, 1B, 2B, 3A, 4A, and 5A of the Periodic Table, as referenced for example, in *Chemistry*, by S. Radel and M. Navidi, West Publishing Company, New York, 1990. Preferred processes include catalytic processes wherein a rare earth element is desirable as a catalyst or catalyst promoter, including without limitation, oxidations, reductions, hydrogenations, isomerizations, aminations, cracking processes, alkylations, esterifications, and other hydrocarbon conversion processes, such as Fischer-Tropsch syntheses. The oxyhalogenation process illustrated herein is only one use for the novel supports described herein; but this illustration should not limit the use of these supports in other applications. Any contacting method can be used to deposit or disperse the catalytic component(s) onto the porous supports of this invention, including without limitation, impregnation, ion-exchange, deposition-precipitation, co-precipitation, and vapor deposition. These contacting methods are well-described in the catalysis art, for example, as may be found in *Fundamentals of Industrial Catalytic Properties*, by Robert J. Farrauto and Calvin H. Bartholomew, Blackie Academic & Professional, an Imprint of Chapman & Hall, London, 1997.

For the instant oxidative chlorination application, the deposition of copper onto the catalyst precursor support, MOX, or catalyst support, $MX_3$, can be accomplished by co-precipitating the copper and lanthanum from a solution containing a base in a manner similar to that noted hereinabove in connection with the formation of the support. Alternatively, the copper can be deposited from a copper-containing solution by impregnation or ion-exchange, or by vapor deposition from a volatile copper compound. Typically, the copper loading is greater than 0.01 weight percent, preferably, greater than 1 weight percent, and more preferably, greater than 5 weight percent, based on the total weight of the catalyst or catalyst precursor composition. Typically, the copper loading is less than 30 weight percent, preferably, less than 20 weight percent, and more preferably, less than 15 weight percent, based on the total weight of the catalyst or catalyst precursor composition.

The oxidative chlorination process of this invention can be conducted in a reactor of any conventional design suitable, preferably, for gas phase processes, including batch, fixed bed, fluidized bed, transport bed, continuous and intermittent flow reactors. Any process conditions (for example, molar ratio of feed components, temperature, pressure, gas hourly space velocity), can be employed, provided that the desired halocarbon product, preferably chlorocarbon, is selectively obtained. Typically, the process temperature is greater than 150° C., preferably, greater than 200° C., and more preferably, greater than 250° C. Typically, the process temperature is less than 500° C., preferably, less than 425° C., and more preferably, less than 350° C. Ordinarily, the process will be conducted at atmospheric pressure or a higher pressure. Typically then, the pressure will be equal to or greater than 14 psia (101 kPa), but less than 150 psia (1,034 kPa). Typically, the total gas hourly space velocity (GHSV) of the reactant feed (hydrocarbon, source of halogen, source of oxygen, and any optional diluent) will vary from greater than 10 ml total feed per ml catalyst per hour ($h^{-1}$), preferably, greater than 100 $h^{-1}$, to less than 50,000 $h^{-1}$, and preferably, less than 10,000 $h^{-1}$.

The chlorocarbon formed in the process of this invention contains a greater number of chlorine substituents than was present in the starting hydrocarbon or starting chlorinated hydrocarbon. The preferred chlorocarbon product is 1,2-dichloroethane. The oxidative chlorination process of this invention produces oxygenated chlorocarbon by-products, such as chloral, in concentrations which are lower by a factor of at least 20 mole percent to as much as 90 mole percent, as compared with prior art oxychlorination processes. Likewise, the oxychlorination process of this invention produces $CO_x$ oxygenates (CO and $CO_2$) in a significantly lower quantity than prior art oxychlorination processes, typically in a quantity lowered by a factor of 10.

The following examples are provided as an illustration of the process of this invention, the catalyst and catalyst precursor compositions of this invention, and the novel supports of this invention. These examples should not be construed as limiting the inventions in any manner. In light of the disclosure herein, those of skill in the art will recognize alternative embodiments, for example of reactants, process conditions, catalyst species, and support species, which all fall within the scope of this invention.

EXAMPLE 1

A catalyst precursor composition comprising copper on a porous lanthanum oxychloride support was prepared as follows. Lanthanum chloride ($LaCl_3 \cdot 7 H_2O$, 15.0 g) was dissolved in deionized water (150 ml). Ammonium hydroxide (6 M, 20 ml) was added to the lanthanum chloride solution quickly with stirring, resulting in a white precipitate. The mixture was centrifuged and the excess liquid decanted yielding a lanthanum-containing gel. Cupric chloride ($CuCl_2 \cdot 2 H_2O$, 0.689 g) was dissolved in ammonium hydroxide (6 M) by using just enough solution to dissolve the copper salt. The copper solution was added to the lanthanum-containing gel. The gel was stirred until a homogeneously colored, dark blue precipitate was obtained. The precipitate was calcined at 400° C. for 4 hours to yield a composition (5.35 g) comprising copper (10 mole percent) dispersed on a porous lanthanum oxychloride support. X-ray diffraction data indicated the presence of a quasi-crystalline form of lanthanum oxychloride. The surface area of the catalyst was 25.8 $m^2/g$, as measured by the BET method.

EXAMPLE 2

The catalyst precursor composition of Example 1 was converted in situ into a catalyst composition of this invention, comprising copper dispersed on a porous lanthanum chloride support. The catalyst was then evaluated in the oxychlorination of ethylene. A tubular reactor was loaded with a mixture of catalyst precursor material (0.3208 g,) from Example 1 and a low surface area alumina diluent (Norton SA5225 alumina; 2.3258 g). The catalyst precursor was dried under a flow of argon at 200° C. for 1 h, then converted in situ to the active catalyst by treating the precursor with a mixture of 44.4 mole percent hydrogen chloride, 8.6 mole percent oxygen, and 47.0 mole percent argon for 10 minutes at 250° C. and with a weight hourly space velocity of 22 $h^{-1}$. The weight hourly space velocity is the mass flow rate divided by the weight of the catalyst tested.

An oxychlorination feed was started comprising 18.2 mole percent ethylene, 36.3 mole percent hydrogen chloride, 7.0 mole percent oxygen, and 38.5 mole percent argon at 250° C. and a weight hourly space velocity of 26 $h^{-1}$. The reaction was continued for 30 minutes at 250° C., and the temperature was changed to 300° C. under the same feed conditions. Results are set forth in Table 1. The measurements at 300° C. in Table 1 were taken using an average of the performance at 300° C. during a 15 minute period. The reaction feed composition was changed to have a lower oxygen content, with 16.7 mole percent ethylene, 33.3 mole percent hydrogen chloride, 4.3 mole percent oxygen, and 45.7 mole percent argon at a weight hourly space velocity of 28 h$^{-1}$. The temperature was raised to 350° C. over 30 minutes and then to 400° C. over 30 minutes. Data in Table 1 taken at 400° C. were an average of the composition during a 15 minute period at 400° C. The gaseous effluent from the reactor was analyzed by mass spectrometry using a calibration matrix to deconvolute the gas composition from the data. Chloral was estimated by monitoring the mass peak at 82 a.m.u. Process conditions and results are set forth in Table 1.

TABLE 1

Oxychlorination of Ethylene to Ethylene Dichloride (EDC)$^a$

| Example | Catalyst | WHSV (h$^{-1}$) | T (° C.) | EDC (ml/min) | Chloral (counts) |
|---------|----------|-----------------|----------|--------------|------------------|
| 2       | Cu/LaCl$_3$ | 26           | 300      | 4.02         | 8                |
| "       | "        | 28              | 400      | 8.86         | 700              |
| CE-1    | Cu/K/Al$_2$O$_3$ | 78      | 300      | 2.84         | 160              |
| "       | "        | 87              | 400      | 7.58         | 900              |

$^a$Oxychlorination feedstream composition (mole percentages): at 300° C., 18.2 percent C$_2$H$_6$, 36.3 percent HCl, 7.0 percent O$_2$, and 38.5 percent Ar; at 400° C., 16.7 percent C$_2$H$_6$, 33.3 percent HCl, 4.3 percent O$_2$, and 45.7 percent Ar. Experiments run at atmospheric pressure.

From Table 1 it is seen that the novel catalyst comprising copper on a porous lanthanum chloride support is capable of oxychlorinating ethylene in the presence of hydrogen chloride and oxygen to 1,2-dichloroethane. As an advantage, only a low level of chloral is produced, especially at the lower reaction temperature of 300° C.

Comparative Experiment 1 (CE-1)

An oxychlorination of ethylene was conducted in the manner described in Example 2, with the exception that a comparative oxychlorination catalyst containing copper (4 weight percent) and potassium (1.5 weight percent) supported on alumina was used in place of the catalyst of Example 2. The comparative catalyst (0.1046 g) was mixed with alumina diluent (2.6639 g), and the mixture was loaded into a reactor similar to that in Example 2. The oxychlorination process was operated as in Example 2, with the process conditions and results set forth in Table 1. When Comparative Experiment 1 is compared with Example 2 at similar process conditions, it is seen that the catalyst of the invention, which comprised copper dispersed on a porous lanthanum chloride support, achieved a higher productivity to 1,2-dichloroethane at a significantly lower selectivity to impurity chloral, as compared with the comparative catalyst.

EXAMPLE 3

The catalyst precursor composition of Example 1 was loaded into a fixed bed reactor, converted into an active catalyst comprising copper on a porous lanthanum chloride support by the in situ method described in Example 2, then tested in the oxychlorination of ethylene. A gas feed containing ethylene (53.75 mole percent), oxygen (14.61 mole percent), and hydrogen chloride (29.26 mole percent) was passed over the catalyst at atmospheric pressure and at 300° C. Flows were adjusted to yield 50 percent conversion of oxygen. The catalyst produced 1,2-dichloroethane as the dominant product. The total carbon oxides (CO$_x$) produced was only 0.8 mole percent of the exit gas. Additionally, since the catalyst was water soluble, the spent catalyst could easily be removed from the reactor and supportive equipment, such as filters and transfer lines, by a simple water wash.

Comparative Experiment 2 (CE-2)

Example 3 was repeated using a comparative oxychlorination catalyst in place of the catalyst of Example 3. The comparative catalyst, similar to the catalyst of experiment CE-1, contained copper (5.7 weight percent) and potassium (1.75 weight percent) supported on alumina. The comparative catalyst produced 1,2-dichloroethane as the dominant product; however, the total carbon oxides (CO$_x$) produced was 4.5 mole percent of the exit gas. When Comparative Experiment 2 was compared with Example 3, it was seen that under similar process conditions the catalyst of the invention produced significantly less carbon oxides than the comparative catalyst.

What is claimed is:

1. A composition of matter comprising copper dispersed on a porous rare earth halide support.

2. The composition of claim 1 wherein the porous rare earth halide support has a BET surface area greater than 5 m$^2$/g.

3. The composition of claim 2 wherein the porous rare earth halide support has a BET surface area greater than 15 m$^2$/g.

4. The composition of claim 1 wherein the rare earth halide support is represented by the formula MX$_3$, wherein M is at least one rare earth lanthanum, cerium, neodymium, praseodymium, dysprosium, samarium, yttrium, gadolinium, erbium, ytterbium, holmium, terbium, europium, thulium, lutetium, or mixtures thereof; or wherein X is chloride, bromide, or iodide.

5. The composition of claim 4 wherein X is chloride, M is lanthanum, and the rare earth halide support is lanthanum chloride.

6. A composition of matter comprising copper dispersed on a porous rare earth oxyhalide support.

7. The composition of claim 6 wherein the porous rare earth oxyhalide support has a BET surface area greater than 12 m$^2$/g.

8. The composition of claim 7 wherein the porous rare earth oxyhalide support has a BET surface area greater than 20 m$^2$/g.

9. The composition of claim 7 wherein the rare earth oxyhalide support is represented by the formula MOX, wherein M is at least one rare earth lanthanum, cerium, neodymium, praseodymium, dysprosium, samarium, yttrium, gadolinium, erbium, ytterbium, holmium, terbium, europium, thulium, lutetium, or mixtures thereof; or wherein X is chloride, bromide, or iodide.

10. The composition of claim 9 wherein X is chloride, M is lanthanum, and the rare earth oxyhalide support is lanthanum oxychloride.

11. A method of using a porous rare earth halide as a catalyst support comprising depositing one or more catalytic components onto the porous rare earth halide support.

12. The method of claim 11 wherein one or more metals or metallic ions are deposited onto the porous rare earth halide support, the metals or metallic ions being the elements of Groups 1A, 2A, 3B, 4B, 5B, 6B, 7B, 8B, 1B, 2B, 3A, 4A, or 5A of the Periodic Table.

13. A method of using a porous rare earth oxyhalide as a catalyst support comprising depositing one or more catalytic components onto the porous rare earth oxyhalide support.

14. The method of claim 13 wherein one or more metals or metallic ions are deposited onto the rare earth oxyhalide support, the metals or metallic ions being the elements of Groups 1A, 2A, 3B, 4B, 5B, 6B, 7B, 8B, 1B, 2B, 3A, 4A, or 5A of the Periodic Table.

15. The method of claim 13 wherein after one or more catalytic components are deposited onto the rare earth oxyhalide support, the support is contacted with a source of halogen under conditions sufficient to convert the rare earth oxyhalide support to a rare earth halide support.

16. The method of claim 15 wherein the source of halogen is hydrogen chloride or molecular chlorine.

* * * * *